United States Patent
Schuster

(10) Patent No.: US 10,517,676 B2
(45) Date of Patent: Dec. 31, 2019

(54) APPARATUS AND COSMETIC METHOD FOR USING SHORT PULSES FOR DERMATOLOGICAL TREATMENTS

(71) Applicant: LUMENIS LTD., Yokneam Ilit (IL)

(72) Inventor: Israel Schuster, Kiryat-Tivon (IL)

(73) Assignee: LUMENIS LTD., Yokneam (IL)

( * ) Notice: Subject to any disclaimer, the term of this patent is extended or adjusted under 35 U.S.C. 154(b) by 96 days.

(21) Appl. No.: 15/221,623

(22) Filed: Jul. 28, 2016

(65) Prior Publication Data

US 2017/0027642 A1   Feb. 2, 2017

Related U.S. Application Data

(60) Provisional application No. 62/200,091, filed on Aug. 2, 2015.

(51) Int. Cl.
*A61B 18/20*   (2006.01)
*A61B 18/00*   (2006.01)

(52) U.S. Cl.
CPC .. *A61B 18/203* (2013.01); *A61B 2018/00005* (2013.01); *A61B 2018/0047* (2013.01); *A61B 2018/00458* (2013.01); *A61B 2018/00476* (2013.01); *A61B 2018/00702* (2013.01)

(58) Field of Classification Search
CPC .................................................. A61B 18/203
USPC .................................... 606/2–19; 607/86–94
See application file for complete search history.

(56) References Cited

U.S. PATENT DOCUMENTS

| | | | | |
|---|---|---|---|---|
| 2002/0087207 | A1* | 7/2002 | Cho | A61B 18/203 607/89 |
| 2010/0014543 | A1* | 1/2010 | Ogilvy | H01S 3/109 372/19 |
| 2013/0172862 | A1* | 7/2013 | Suckewer | A61B 18/203 606/9 |
| 2014/0121631 | A1* | 5/2014 | Bean | A61N 5/0616 604/500 |
| 2015/0366611 | A1* | 12/2015 | Rosenberg | A61B 18/18 606/9 |

* cited by examiner

*Primary Examiner* — Carl H Layno
*Assistant Examiner* — Dacheng Xie
(74) *Attorney, Agent, or Firm* — ISUS Intellectual Property PLL; Anthony Jason Mirabito

(57) ABSTRACT

A cosmetic method of treating skin tissue with a laser source includes applying a plurality of short pulses of predetermined parameters to ramp up the temperature of the skin tissue to reach a desired temperature and then applying a plurality of short pulses to maintain a temperature dwell time. The predetermined parameters are selected from one or more of: pulse peak power, pulse duration, pulse repetition rate and laser wavelength.

3 Claims, 3 Drawing Sheets

APPARATUS AND COSMETIC METHOD FOR USING SHORT PULSES FOR DERMATOLOGICAL TREATMENTS

RELATED APPLICATIONS

This application is related to and claims priority to U.S. Provisional Application No. 62/200,091, filed Aug. 2, 2015, the entire contents of which are herein incorporated by reference.

FIELD OF THE INVENTION

This invention is directed to an apparatus and cosmetic method of, among other things, hair removal using light-based technologies, with the goal, in the case of hair removal, is to remove hair without overheating and causing pain or discomfort to the skin tissue of the patient.

BACKGROUND OF THE PRESENT INVENTION

Today, it is common practice to utilize lasers in dermatological treatments by the use of long single pulses (of about a few milliseconds) at a constant power or a train of pulses. In most such cases, this kind of treatment is accompanied with the application of local cooling of the area of the skin tissue which is treated. This method, although considered effective for many skin types, is usually not considered safe for treating people with dark skin as it might produce severe burns.

FIGS. 1A and 1B represent simulations of a laser assisted hair removal process with skin type IV (FIG. 1A) and skin type VI (FIG. 1B). Skin types are conventionally categorized as levels I through VI in dermatological practice using the Fitzpatrick scale, the higher the number being the darker the skin tone. In FIGS. 1A and 1B, the temperature of the hair follicle as well as the temperature of the epidermis at various levels can be seen. The treatment parameters that were used in the simulation for skin type IV have been proven to be both safe and effective. The obtained temperatures in the hair follicle are very high while maintaining the skin temperature at acceptable temperature levels. When trying to obtain even smaller temperature levels of hair follicle in type VI skin (which additionally has the disadvantage of less efficacy), the epidermis temperature increased to dangerous levels, as shown in FIG. 1B.

In another known approach, known as bulk heating, the laser system made to emit a continuous pulse sequence (such as, for example, 10 Hz 20 ms); the clinician glides the treatment head over an extended treated area, causing a gradual temperature increase in this area by repeated "visits" at the same spots. This method is typically applied with very mild cooling. Although safer than the method discussed previously when treating dark skin, it is considered less effective, especially when treating light hair or when trying to treat specific glands.

SUMMARY OF THE PRESENT INVENTION

Figure 1B:
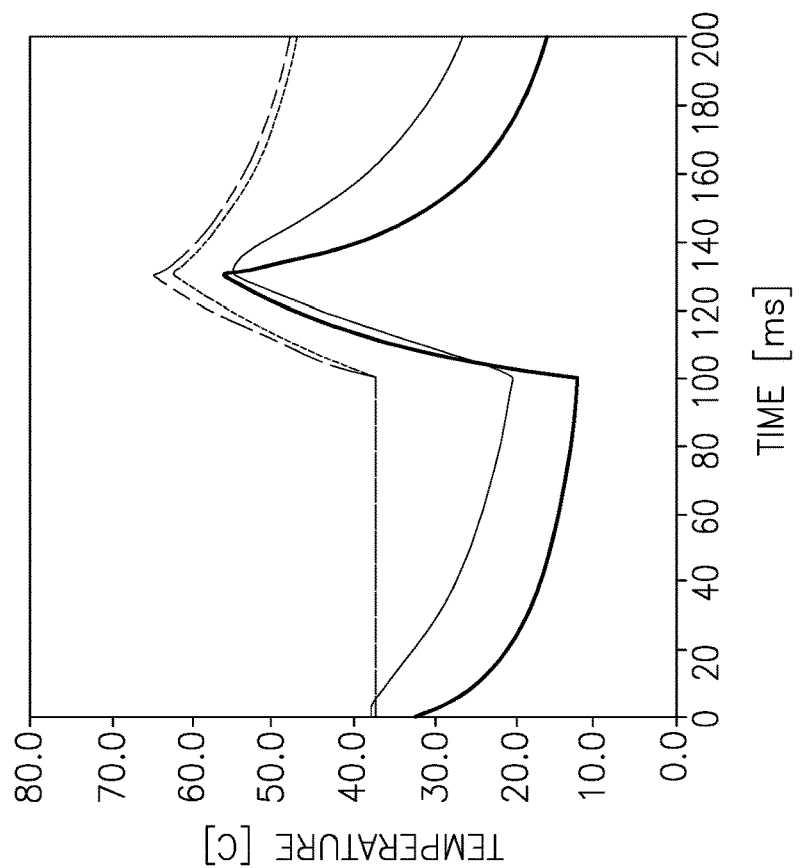
FIGS. 1A and 1B illustrate simulations of prior art laser treatments as applied to the skin tissue of patents of skin types IV and VI respectively.

In an aspect, a cosmetic method of treating skin tissue with a laser source includes applying a plurality of short pulses of predetermined parameters to ramp up the temperature of the skin tissue to reach a desired temperature and then applying a plurality of short pulses to maintain a temperature dwell time. The predetermined parameters are selected from one or more of: pulse peak power, pulse duration, pulse repetition rate and laser wavelength.

In another aspect, the cosmetic method includes the step of cooling the skin tissue one or more of before, during and after the applying of the short pulses.

The short pulses may have a range, in an exemplary application of hair removal, of from 0.1 ms to 5 ms during ramp up and during temperature dwell time, or the pulses may be different during the ramp up and temperature dwell time. In addition, the pulse repetition rate may range between 100 Hz to 200 kHz and peak power may range from 1500 W to 8000 W. The above examples may be varied as needed or desired in terms of the treatment given and the anatomy of the particular patient upon whom a procedure is be performed. For other dermatological applications, such as those mentioned herein, the parameters of application may and could likely be different from those given above.

In a further aspect, the cosmetic method further includes a programmed controller to control the application of the laser to produce the short pulses. The programmed controller further controls a cooling device such that after ramp up, cooling of the skin tissue causes the temperature on the epidermis of the skin to be lower than the temperature of a hair follicle. Also, the controller controls the laser source to apply power to be higher during the ramp up time than during the subsequent dwell time.

In yet a further aspect, the short pulses may have a repetition rate from about 100 Hz to about 3 kHz and may range in peak power levels from about 1500 W to about 8000 W. The short pulses during ramp up and temperature dwell time may be different.

In another aspect, the method of treating skin tissue is for the purpose of one or more of: hair removal, treatment of hyperhidrosis, treatment of acne and treatment of vascular lesions.

DETAILED DESCRIPTION OF THE PRESENT INVENTION

One aim of present invention is to improve the safety and efficacy of dermatologic laser treatments. This is accomplished by providing the required temperature level to the skin tissue(s) to be treated for the required amount of time to cause apoptosis or necrosis of targeted tissue(s), with minimal effect on other tissues.

To obtain effective results with a specific type of tissue, it is desirable to increase the temperature of that tissue to a certain level and then maintain the tissue at this temperature for some time (which is tissue dependent). This is known as dwell time. A schematic description of such a temperature profile is presented in FIG. 2A. To obtain effective treatment results, it may be important to maintain dwell temperatures for sufficiently long enough dwell times to produce the desired results (Michael L. Denton; Gary D. Noojin; B. Giovanna Gamboa; Elharith M. Ahmed; Benjamin A. Rockwell; Photothermal damage is correlated to the delivery rate of time-integrated temperature. Proc. SPIE 9706, Optical Interactions with Tissue and Cells XXVII, 97061M (Mar. 7, 2016); doi: 10.1117/12.2225024.). It has been found that higher temperature levels of application for shorter periods of time, may not produce similar desirable effects on the skin tissue as long dwell times.

Figure 2A:
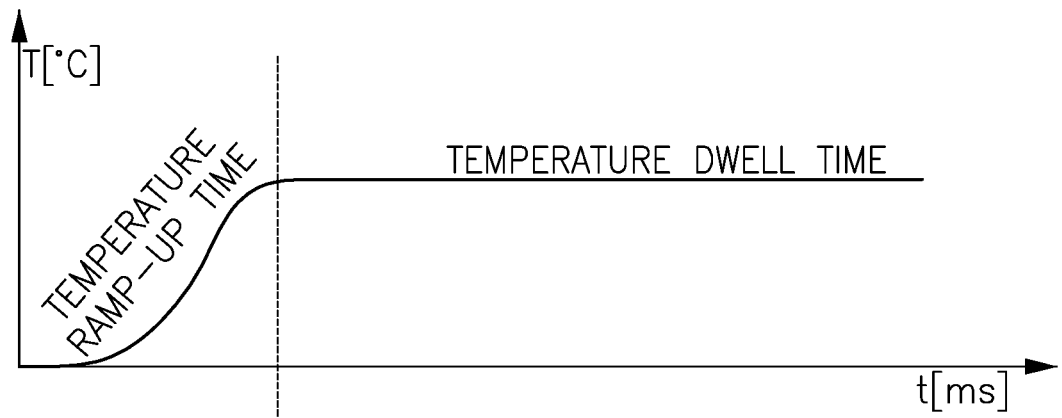
FIGS. 2A and 2B graphically illustrate temperature ramp up time and temperature dwell time.
Figure 2B:
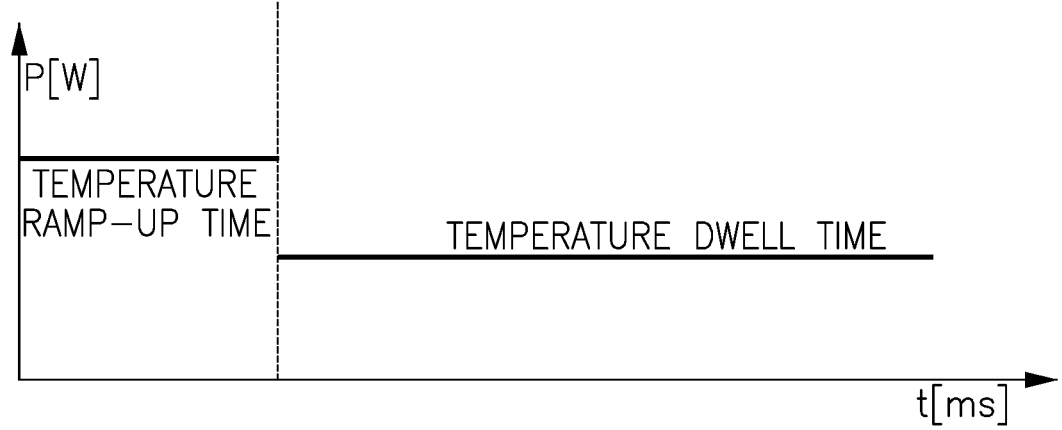

To obtain such a temperature profile shown in FIG. 2A, high laser power level may be applied to the skin tissue during the temperature rise or ramp up time shown in FIG. 2A and subsequently lower laser power to maintain the type of constant dwell temperature illustrated in FIG. 2A. During skin treatment accompanied by epidermal cooling as is known to those skilled in the art, the temperature of the epidermis will rise during the temperature ramp-up time but then will maintain or even decrease its temperature during the dwell time, as can be seen in FIG. 2B. This effect increases the temperature level selectivity between the inner tissue and the epidermis, allowing safe treatment of dark skin types while obtaining higher efficacy. It has been found that once the temperature dwell time has been reached, the applied cooling takes over and keeps the temperature in the epidermis at acceptable levels.

To further increase treatment efficacy and selectivity, the present invention uses short laser pulses to obtain the desired ramp-up time and temperature and keep the temperature level during the dwell time as long as may be desired or required. There are three laser pulse parameters that can be controlled and implemented in order to obtain the desired temperature levels and ramp-up time: pulse peak power, pulse duration, and pulse repetition rate. By selectively adjusting among these parameters, good selectivity to the epidermis can be obtained as well as good selectivity between tissues within the same treatment zone (glands, organs, tissues), depending on their specific thermal relaxation times and the absorption efficiency of the laser wavelength (which is also a parameter for enhancing selectivity). Another advantage of employing a plurality of short pulses is that "overshooting" is prevented or at least substantially reduced due to the control that can be exercised using short pulses. Overshooting can cause excessive temperature rises that may cause discomfort or pain or even damage tissues, such as the epidermis. A suitable programmed or programmable controller may be employed to exercise control over the above parameters and even display graphically on a suitable user interface the applied pulses.

Figure 1A:
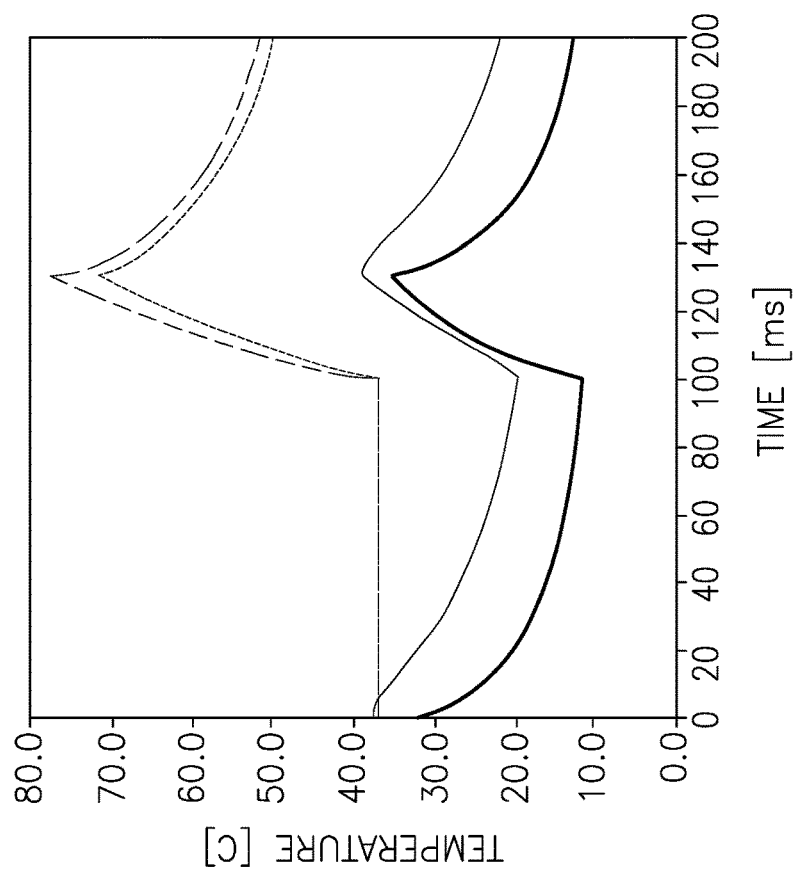
Figure 3B:
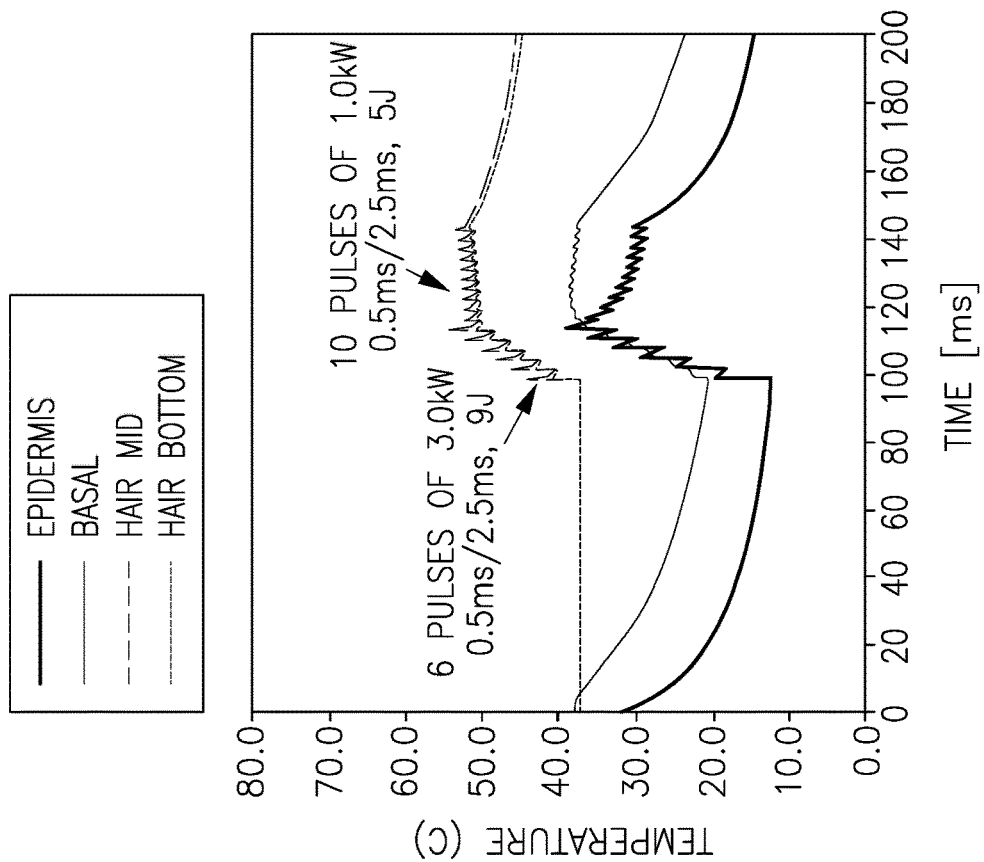
FIGS. 3A and 3B illustrate simulations of laser treatments as applied the skin tissue of patents of skin types IV and VI respectively using the present invention.
Figure 3A:
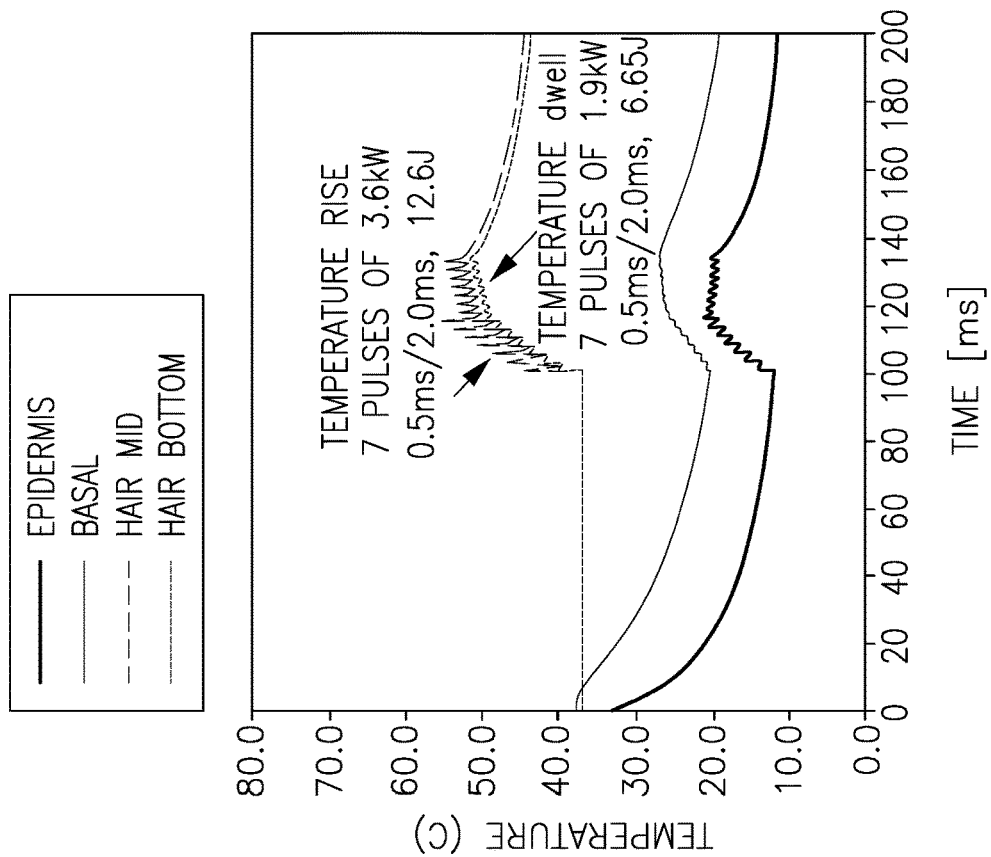

While usage of short pulses to increase selectivity between two adjacent organs may be known in other environments (Mark A. Latina, U.S. Patent 005549596A; Charles P. Lin, U.S. Pat. No. 7,115,120B2), the combination with the pulse sequence and dwell time to obtain the simultaneous selectivity to the cooled epidermis layer is believed to be not known. A simulation of such pulse sequence is illustrated in FIGS. 3A and 3B, in which, as in FIGS. 1A and 1B, hair removal treatments applied to skin type IV (FIG. 3A) versus skin type VI (FIG. 3B) is shown. In this example, 0.5 ms pulses were used for both treatments. The peak power was 3.6 kW and 1.9 kW during ramp-up and dwell times respectively for skin type IV. Pulse period was 2.0 ms (repetition rate of 500 Hz). The differences between the results of FIGS. 3A and 3B and FIG. 1A are quite evident from comparing the graphs. For skin type VI, 3.0 kW and 1.0 kW peak power were applied during ramp-up and dwell times respectively, and the pulse period was 2.5 ms (repetition rate of 400 Hz). One can see that the effect of applying the pulse trains shown resulted in a temperature decrease in the epidermis) while maintaining the hair follicle temperature during dwell time. The dwell time can be made to be as long as desired or needed. The pulse periods above, the peak power applied as set forth in FIGS. 3A and 3B are merely exemplary settings and the invention herein should not be considered as limited to the given examples. The frequency of the pulses, the power applied for each pulse, and other parameters can be selected as required depending on the skin type, the desired effects, and the like in order to produce the desired effects, all of which can be under the control of the programmed controller.

The methods described above are not limited to any specific laser apparatus and thus method can be implemented in various laser treatments where cooling of the surface layer is applied. Dermatologic applications include but are not limited to: hair removal (by targeting the hair follicle), hyperhidrosis (by targeting the sweat gland), acne (by targeting the sebaceous gland), vascular lesions (by targeting blood vessels of various sizes), pigmented lesions (by targeting melanin and melanocytes) and more. Obviously, proper laser wavelength selection ensures farther enhancement of treatment selectivity.

What I claim is:

1. A cosmetic method of treating skin tissue for hair removal with a laser source comprising: (a) applying a first plurality of short pulses of pulse width 0.5 ms and repetition rate of one of 500 Hz or 400 Hz of predetermined parameters at a predetermined power level X to ramp up the temperature of the skin tissue to reach a desired dwell time temperature and (b) applying a second plurality of short pulses of pulse width 0.5 ms at a predetermined power level x, wherein x<X to maintain the desired dwell time temperature; and, controlling, using a programmed controller, the application of the laser source to produce the short pulses of (a) and then (b); and further comprising, using the programmed controller, controlling a cooling device, after ramp up to the desired temperature, to cool the skin tissue, during the dwell temperature time only, to cause the temperature on the epidermis of the skin to be lower than the temperature of a hair follicle level within the skin tissue.

2. The cosmetic method of claim 1, wherein the predetermined parameters are selected from one or more of: pulse peak power, pulse duration, pulse repetition rate and laser wavelength.

3. The cosmetic method of claim 1, wherein the short pulses range in peak power levels from about 1500 W to about 8000 W.

* * * * *